United States Patent [19]
Coen et al.

[11] Patent Number: 5,914,244
[45] Date of Patent: Jun. 22, 1999

[54] UL97 FUSION PROTEINS AND METHODS OF USE

[75] Inventors: Donald M. Coen, Medfield; Zuwen He, Framington, both of Mass.

[73] Assignee: President and Fellows of Harvard College, Cambridge, Mass.

[21] Appl. No.: 08/910,484

[22] Filed: Jul. 25, 1997

Related U.S. Application Data

[60] Provisional application No. 60/022,888, Jul. 26, 1996.

[51] Int. Cl.$^6$ .............................. C12Q 1/48; C12Q 1/00; G01N 33/53
[52] U.S. Cl. .............................. 435/15; 435/4; 435/975; 435/320.1; 424/9.34; 424/93.2; 530/300; 530/387
[58] Field of Search .............................. 435/15, 4, 975, 435/320.1; 424/9.34, 93.2; 530/300, 387

[56] References Cited

PUBLICATIONS

Britt, William J., "Human Cytomegalovirus Virion–Associated Protein with Kinase Activity", *Journal of Virology*, Jul. 1986, pp. 185–188.

Chee, M.S., et al., Alpha–, Beta– and Gammaherpesviruses Encode a Putative Phosphotransferase, *J. gen. Virol.*, 1989, pp. 1151–1160.

Coulter, L.J., et al., "A mutant of herpes simplex virus type 1 in which the UL13 protein kinase gene is disrupted", *Journal of Gen. Virology*, 1993, pp. 387–395.

De Wind, Niels, et al., "Herpesviruses Encode an Unusual Protein–Serine/Thereonine Kinase Which is Non–Essential for Growth in Cultured Cells", *Journal of Virology*, Sep. 1992, pp. 5200–5209.

Edelman, Arthur M., "Protein Serine/Threonine Kinases", *Ann. Rev. Biochem.*, 1987, pp. 567–613.

Hanks, Steven K., "The Protein Kinase Family: Conserved Features and Deduced Phylogeny of the Catalytic Domains", *Science*, vol. 241, pp. 42–52. (Jul. 1988).

Heineman, Thomas C., "The Varicella–Zoster Virus (VZV) Open Reading Frame 47 (ORF47) Protein Kinase is Disp. for Viral Replication and is Not Required for Phosphorylation of ORF63 Protein, the VZV Homolog of Herpes Simplex Virus ICP22", *Journal of Virology*, Nov. 1995, pp. 7367–7370.

Hubbard, Stevan R., "Crystal structure of the tyrosine kinase domain of the human insulin receptor", *Nature*, vol. 372, Dec. 22/29, 1994, pp. 746–754.

Knighton, Daniel R., et al., "Crystal Structure of the Catalytic Subunit of Cyclic Adenosine Monophosphate–Dependent Protein Kinase", *Science*, Jul. 26, 1991, pp. 407–414.

Mar, Eng–Chun, et al., Human Cytomegalovirus–associated DNA Polymerase and Protein Kinase Activities, *Journal of Gen. Virology*, 1981, 57, pp. 149–156.

Michelson, Susan, et al., "Catalytic properties of a human cytomegalovirus–induced protein kinase", *Eur. J. Biochem*, Feb. 1985, 149, pp. 393–399.

Michelson, S., et al., "Properties of a Human Cytomegalovirus–Induced Protein Kinase", *Virology*, 1984, pp. 259–268.

Overton, Hilary, et al., "Production of Host Shutoff–Defective Mutants of Herpes Simplex Virus Type 1 by Inactivation of the UL13 Gene", *Virology*, 202, 1994, pp. 97–106.

Pearson, Richard B., et al., "Autoregulation of Enzymes by Pseudosubstrate Prototypes: Myosin Light Chain Kinase", *Science*, vol. 241, pp. 970–973, (Aug. 1988).

Roby, Clinton, et al., "Characterization of Phosphoproteins and Protein Kinase Activity of Virions, Non–infectious Enveloped Particles, and Dense Bodies of Human Cytomegalovirus", *Jour. of Virol*, Sep. 1986, pp. 714–727 (1980).

(List continued on next page.)

*Primary Examiner*—Louise N. Leary
*Attorney, Agent, or Firm*—Fish & Richardson P.C.

[57] ABSTRACT

Soluble, enzymatically active CMV UL97 and methods of detecting inhibitors and enhancers of its ability to phosphorylate are disclosed.

19 Claims, 7 Drawing Sheets

OTHER PUBLICATIONS

Sullivan et al., "A protein kinase homologue controls phosphorylation of ganciclovir in human cytomegalo–virus–infected cells", *Nature*, Jul. 9, 1992, vol. 358, pp. 162–164.

Sullivan et al., Erratum: "A protein kinase homologue controls phosphorylation of ganciclovir in human cytomegalovirus–infected cells", *Nature*, Sep. 3, 1992, vol. 359, p. 85.

Sullivan et al., Erratum: A protein kinase homologue controls phosphorylation of ganciclovir in human cytomegalovirus-infected cells, *Nature*, Dec. 23/30, 1993, vol. 366, pp.756.

Sullivan et al., A point mutation in the human cytomegalovirus DNA polymerase gene confers resistance to ganciclovir and phosphonylmethoxyl alkyl derivatives, *Antimicrob. Agents & Chemo*. Jan. 1993 vol.37 No.1, pp. 19–25.

Van Zeijl et al., The human cytomegalovirus UL97 protein is phosphorylated and a component of virions, *Virology*, 1997, vol. 231, pp. 72–80. Month not available.

Rawlinson et al., The murine cytomegalovirus (MCMV) homolog of the HCMV phosophotransferase (UL97(pk)) gene *Virology*, 1997, vol. 233, pp. 358–363. Month not available.

International Search Report of PCT/US97/13340 dated Oct. 7, 1997 (6 pp.).

He et al; Jour. of Virology; vol. 71(1); pp. 405–411, Jan. 1997.

UL97 FUSION PROTEINS AND METHODS OF USE

CROSS REFERENCE TO RELATED APPLICATION

This application claims benefit from provisional application Ser. No. 60/022,888, filed Jul. 26, 1996.

STATEMENT AS TO FEDERALLY FUNDED RESEARCH

This invention was supported in part U.S. Public Health Service grant number UO1A126077. The government may therefore have certain rights in the invention.

FIELD OF THE INVENTION

The invention relates to protein kinases and assays for the detection of agents that enhance or inhibit protein kinase activity.

BACKGROUND OF THE INVENTION

Human cytomegalovirus (CMV) is a beta herpesvirus that causes significant pathology in individuals who are immunosuppressed, e.g., organ transplant recipients or individuals with Acquired Immune Deficiency Syndrome. There have been several reports of protein kinases induced by or associated with CMV infection. Mar et al., *J. Gen. Virol.* 57:149–156 (1981); Michelson et al., *Eur. J. Biochem.* 149:393–399 (1985); Michelson et al., *Virology* 134:259–268 (1984); Roby et al., *J. Virol.* 59:714–727 (1986); Britt et al., *J. Virol.* 59:185 (1986). UL97 is a CMV gene which is homologous to protein kinases. Chee et al., *J. Gen. Virol.* 70:1151–1160 (1989). An apparent substrate for UL97 is Ganciclovir (GCV), a nucleoside analog that has been used to inhibit CMV replication. GCV must be phosphorylated in order to be active. The UL97 gene product has been shown to be responsible for phosphorylation of GCV in CMV-infected cells, as a mutation in UL97 renders infected cells GCV resistant ($GCV^r$), and also results in decreased GCV phosphorylation. Baldanti et al., *J. Virol.* 69:796–800 (1995); Hanson et al., *Antimicrob. Agents Chemother.* 39:1204–1205 (1995); Lorain et al., *J. Virol.* 68:4427–2231 (1994); Sullivan et al., *Nature* 358:162–165 (1992). UL97, when expressed in heterologous systems, can induce GCV phosphorylation in the absence of other CMV proteins. Littler et al., *Nature* 358:160–162 (1992); Metzger et al., *J. Virol.* 68:8423–8427 (1994). Extracts of *E. coli* expressing UL97 can phosphorylate GCV, and antiserum to a UL97 extract that has been partially purified from *E. coli* can immunoprecipitate GCV kinase activity from extracts of CMV-infected human cells. Littler et al., supra. Thus, it appears that UL97 mutations confer resistance to GCV by impairing the GCV kinase activity of UL97.

CMV UL97 is most closely related in sequence to a family of proteins encoded by all known herpesviruses. Chee et al., *J. Gen. Virol.* 70:1151–1160 (1989); deWind et al., *J. Virol.* 66:5200–5209 (1992); Smith et al., *J. Virol.* 63:450–455 (1989). HSV UL13, VZV ORF 47, and pseudorabies virus (PRV) UL13 are all associated with protein kinases. However, of these, only the PRV UL13 protein has been shown to be active when expressed in a heterologous system (de Wind et al., *J. Virol.* 64:4691–4696 (1990)); neither HSV UL13 nor VZV ORF 47 has exhibited activity following heterologous expression (Ng et al., *Virology* 191:9–18; Stevenson et al., *J. Gen. Virol.* 75:317–326 (1994)), and none of these proteins has yet been purified to show that it does not require any cellular proteins as cofactors.

Of the approximately twenty $GCV^r$ UL97 mutants that have been described, none appears to be a null mutant; i.e., no nonsense or frameshift mutations have been identified. Known UL97 mutations resulting in GCV resistance fall into two general classes. In one class, a segment of the UL97 protein that corresponds to a portion of the cAMP-dependent protein kinase that is involved in substrate specificity is affected. In the other class, the mutations map to a residue within a conserved region in UL97 that corresponds to the catalytic loop, but this particular residue is also implicated in substrate recognition. Thus, phosphorylation of GCV, which appears to be a fortuitous substrate of UL97, could be drastically impaired without major effects on phosphorylation of natural substrates of UL97. Accordingly, UL97 may be essential for CMV replication, and thus an important target for inhibition by antiviral drugs.

GCV has been widely used to treat CMV infection. However, GCV and other known anti-CMV drugs are limited by toxicity, pharmacokinetic problems, and/or lack of potency or efficacy in various settings. Moreover, GCV resistance in CMV-infected cells in vivo is a substantial problem. Biron, *International Antiviral News* 2:117–118 (1994); Drew et al., *J. Infect. Dis.* 163:716–719 (1991); Erice et al., *New Engl. J. Med.* 320:289–293 (1989); Tatarowicz et al., *J. Infect. Dis.* 166:904–907 (1992). It would therefore be desirable to develop screening assays for the identification of drugs that affect CMV infection and the pathology resulting therefrom.

SUMMARY OF THE INVENTION

The invention is based on the high level expression of soluble active UL97 proteins, and the finding of substrates for these proteins.

The invention features isolated nucleic acids encoding UL97 or UL97 fusion proteins. As used herein, "UL97 fusion protein" means a polypeptide consisting of some or all of the UL97 protein linked to a heterologous polypeptide sequence, and which encodes a soluble, enzymatically active protein, i.e., a protein with the ability to autophosphorylate and/or to phosphorylate other substrates. A UL97 fusion protein contains at least 30%, preferably 50%, more preferably 75% and most preferably 85% or more of the full length UL97 gene product. The nucleic acids encoding these fusion proteins include sequences encoding at least a part of a UL97 gene linked to sequences encoding a heterologous polypeptide. The nucleic acids of the invention contain sequences encoding at least 30%, preferably 50%, more preferably 75% and most preferably 85% or more of the full length UL97 gene product.

The nucleic acids of the invention can be genomic DNA, cDNA or RNA. In one embodiment, the nucleic acid encodes a glutathione-S-transferase (GST)-UL97 fusion protein. As used herein, "isolated" means nucleic acid that has been extracted from cells by any one of a number of methods which are well known to those skilled in the art. Isolated nucleic acids include recombinant DNA that is incorporated into a vector (e.g., an autonomously replicating virus or plasmid), or into the genomic DNA of a prokaryote or a eukaryote, as well as DNA which exists as a separate molecule independent of other DNA sequences such as a cDNA or genomic DNA fragment produced by chemical means (e.g., polymerase chain reaction or ligase chain reaction), or by restriction endonuclease treatment.

The isolated nucleic acids of the invention can be incorporated into clones or lines of essentially homogeneous populations of cells. Preferably, at least 90% of the cells contain the vector or the isolated nucleic acid of the invention; more preferably, at least 99% of the cells contain the vector or isolated nucleic acid of the invention.

The invention also features a substantially pure preparation of UL97 or a UL97 fusion protein. In one embodiment, the fusion protein is a glutathione-S-transferase (GST)-UL97 fusion protein. In addition, the invention includes a fragment of UL97 or a UL97 fusion protein which is capable of phosphorylating itself or other substrates. The invention also includes a method of purifying an enzymatically active, soluble UL97 protein or UL97 protein fragment or UL97 fusion protein.

As used herein, a "substantially pure" preparation of a protein is substantially free from the components that naturally accompany it. Typically, a preparation is substantially pure when at least 85%, more preferably at least 90%, more preferably at least 95%, and most preferably at least 99% of the total material (by weight) in a sample is composed of the protein of interest.

In another aspect, the invention is an assay for the detection of substrates which can be phosphorylated by the CMV UL97 protein kinase. The assay includes the steps of incubating a substance which may be a UL97 substrate with a UL97 protein kinase, adding a phosphate source, and measuring phosphorylation of the substance. A substance is a substrate if measurable phosphorylation is detected in the assay, e.g., if an increase in incorporation of radioactive phosphate is detected. Such an increase is an increase of at least 100% over background radioactivity, i.e., the radioactivity detected in the absence of UL97; preferably, 200% over background; more preferably, 500% over background; more preferably, 1000% over background. The term "UL97 protein kinase" includes any polypeptide, including a fusion protein or a protein fragment, which contains an active portion of the UL97 protein; i.e., a portion of the UL97 protein that can phosphorylate a UL97 substrate.

In another aspect, the invention is an assay for the detection of an agent which inhibits UL97 protein kinase activity. Such agents would be useful in, e.g., decreasing phosphorylation of substrates which are activated by phosphorylation and exacerbate the pathological effects of CMV infection. The assay includes the steps of:

a) providing a substrate for UL97 protein kinase;
b) incubating said substrate with UL97 protein kinase to form a substrate-protein kinase reaction mixture;
c) adding a phosphate source;
d) adding a potential inhibitor of UL97 protein kinase activity to said reaction mixture;
e) measuring the amount of phosphorylation of said substrate in said reaction mixture; and
f) comparing the amount of phosphorylation of said substrate detected in step (e) with the amount of phosphorylation detected in the absence of said potential inhibitor, as a measure of the inhibition of UL97 protein kinase activity.

An agent which "inhibits" UL97 protein kinase activity causes a decrease in the phosphorylation of a known UL97 substrate. This decrease can be measured by, e.g., a decrease in the incorporation of radioactive phosphate into the UL97 substrate compared to the amount of radioactive phosphate incorporated in the absence of the agent. Phosphorylation is preferably decreased by 50%, more preferably by 70%, more preferably 80%, and more preferably 90% or more.

The substrate used in the assay can be a histone preparation, histone H1, histone H2B or any peptide or polypeptide containing an amino acid sequence that corresponds to a UL97 consensus phosphorylation sequence. A "UL97 consensus phosphorylation sequence" is a five to thirty amino acid sequence containing a residue which is phosphorylated by UL97 and which is flanked by some or all of the amino acid residues most commonly found to surround this residue.

The invention also includes an assay for the detection of an agent which enhances UL97 protein kinase activity. Such agents would be useful, e.g., in increasing phosphorylation of GCV. The assay includes the steps of:

a) providing a substrate for UL97 protein kinase;
b) incubating said substrate with UL97 protein kinase to form a substrate-protein kinase reaction mixture;
c) adding a phosphate source;
d) adding a potential enhancer of UL97 protein kinase activity to said reaction mixture;
e) measuring the amount of phosphorylation of said substrate in said reaction mixture; and
f) comparing the amount of phosphorylation of said substrate detected in step (e) with the amount of phosphorylation detected in the absence of said potential enhancer, as a measure of the enhancement of UL97 protein kinase activity.

An agent which "enhances" UL97 protein kinase activity causes an increase in the phosphorylation of a known UL97 substrate. This increase can be measured by, e.g., an increase in the incorporation of radioactive phosphate into the UL97 substrate compared to the amount of radioactive phosphate incorporated in the absence of the agent. Phosphorylation is preferably increased by 50%, more preferably by 100%, more preferably 200%, and more preferably 500% or more.

The substrate used in the assay can be a histone preparation, histone H1, histone H2B, or any peptide or polypeptide containing a UL97 consensus phosphorylation sequence.

In a further aspect, the invention is a high throughput screen (HTS) for the detection of agents that inhibit or enhance UL97 protein kinase activity. In one embodiment, the substrate for the HTS is a peptide or polypeptide containing a UL97 consensus phosphorylation sequence. The HTS includes the steps of:

a) isolating a peptide or polypeptide containing a UL97 phosphorylation site and residues which allow binding to a solid support which contains a plurality of individual chambers, e.g., a 96 well plastic tissue culture plate;
b) binding the peptide or polypeptide to the chambers of the solid support;
c) adding purified UL97 and a phosphate source to the chambers of the solid support;
d) adding potential inhibitors or enchancers of UL97 phosphorylation to the chambers; and
e) measuring the amount of phosphorylation in the presence of the potential inhibitor or enhancer, and comparing the value obtained to that obtained in the absence of the suspected inhibitor or enhancer. The HTS can be automated to achieve greater effeciency.

In another aspect, the invention is a kit for the detection of agents that inhibit or enhance UL97 protein kinase activity. The kit includes a reaction vessel; a substantially pure UL97 protein kinase; and a substrate that is capable of being phosphorylated by UL97.

The invention also includes a peptide or a polypeptide containing a UL97 phosphorylation consensus sequence.

This peptide or polypeptide can be modified so that its administration affects CMV infection. A peptide is "modified" by, for example, conversion of serine to a non-phosphorylatable group (See, e.g., Cheng et al., *Biochem. J.* 231, 655 (1986); Kemp, ed. *Peptides and Protein Phosphorylation*, CRC Press, Boca Raton, Fla. (1990)), especially if it imparts tighter binding; linkage of the peptide to residues from the tat protein of human immunodeficiency virus, as described in Fawell et al., *Proc. Natl. Acad. Sci.*, 91:664 (1994) and Pepinsky et al., *DNA and Cell Biology*, 13:1011 (1994); and/or conversion of peptides to non-peptide analogs as described in, e.g., Liuzzi et al., *Nature* 372:695 (1994).

Modified or unmodified peptides or polypeptides of the invention can also be formulated into a pharmaceutical composition for the treatment of CMV infection. The invention includes a method of treating CMV infection by administering a therapeutically effective amount of the pharmaceutical composition to a CMV-infected individual.

Unless otherwise defined, all technical and scientific terms used herein have the same meaning as commonly understood by one of ordinary skill in the art to which the invention pertains. All publications mentioned herein are incorporated by reference. The examples which follow are illustrative only, and not intended to be limiting.

Other features and advantages of the invention will be apparent from the detailed description, and from the claims.

DETAILED DESCRIPTION

UL97 is a CMV gene which encodes a protein kinase. In order to characterize UL97, antiserum reactive to UL97 has been developed. UL97 and UL97 fusion proteins have been expressed in baculovirus-infected insect cells, and purified to homogeneity. UL97 can phosphorylate itself on serine and threonine residues. At least one GCV-resistance mutation drastically impairs GCV phosphorylation, without major effects on autophosphorylation.

An assay has been developed to identify substrates for UL97. Using this assay, exogenous substrates which can be phosphorylated by UL97 have been identified. Assays that exploit UL97'S ability to phosphorylate exogenous substrates have been developed to detect agents that inhibit or activate UL97, and which would therefore be useful in the treatment of CMV infection and the accompanying pathology.

Materials and Methods

Cells and Viruses

Laboratory wild-type CMV strain AD169 and human foreskin fibroblast (HFF) cells were propagated as previously described (Sullivan et al., *J. Infect. Dis.* 164:781–784 (1991). *Spodoptera Frugiperda Sf9* and *Sf*21 cells were obtained from Invitrogen and maintained in Grace's insect medium (BioWhitaker) supplemented with 10% fetal calf serum, 100 IU/ml penicillin and 100 µg/ml streptomycin. Recombinant baculoviruses derived from baculoviruses derived from *Autographia californica* nuclear polyhidrosis virus (AcNPV) were propagated using standard methods (Summers et al., "A Manual for Method of Baculovirus Vectors and Insect Cell Culture Procedures," Texas Agricultural Experiment Station, College Station, 1987).

Expression of maltose-binding protein/UL97 fusion protein (MBP-UL97) in *E. coli*

Figure 1:
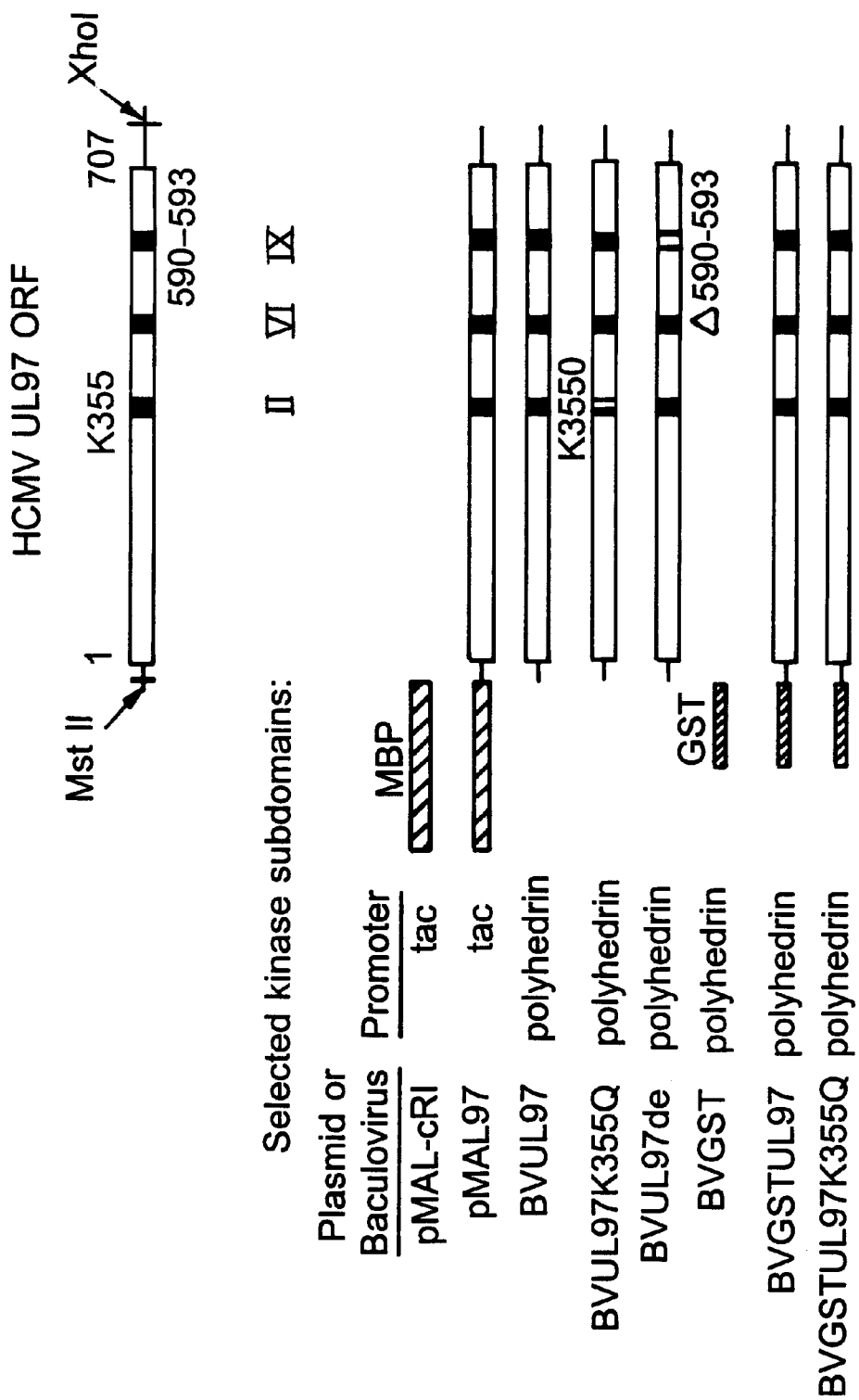
FIG. 1 is a diagram showing various control and UL97 recombinant constructs.

Constructs containing wild type and mutant forms of UL97 are shown schematically in FIG. 1. The top line indicates the UL97 open reading frame as an open box. The locations of restriction sites for MstII and XhoI that flank the open reading frame are shown. Segments of UL97 corresponding to protein kinase subdomains II, VI, and IX (Hanks et al., *Science* 241:42–52 (1988)) are indicated as filled boxes and the positions of lysine 355 (K) and residues 590–593, which are altered in mutant forms of UL97, are shown. Below are diagrammed the plasmids or baculoviruses used for expression of UL97. The top two plasmids were used for expression in *E. coli*, and the remaining constructs for construction of recombinant baculoviruses. The promoter sequences used are indicated (tac for bacterial expression, polyhedrin for baculovirus expression). Fusion partners are designated by hatched boxes for MBP and shaded boxes for GST. The UL97 open reading frame is cartooned as an open box. The positions of the K355Q UL97 mutation is designated by K335Q and a shaded box in place of a filled box and the four-codon deletion from mutant 759ʹD100 by Δ590–593 in an open box (replacing a filled box) when these mutations are present. The constructs were generated as follows.

In order to generate an expression vector containing a gene encoding a UL97 fusion protein, the UL97 open reading frame (ORF) was isolated from cosmid pCM1065 (Fleckenstein et al., *Gene* 18:39–46 (1982)) by digestion with EcoRI and HindIII. A 3.5 kb EcoRI-HindIII fragment (corresponding to positions 9,415–12,913 in the AD169 strain of CMV) containing the UL97 ORF was isolated and cloned into pGEM7Z f(+) (Promega) to generate plasmid pADEH. A 2.25 kb fragment (corresponding to positions 10,376–12,632 in the AD169 strain of CMV), obtained by digestion of pADEH with MstII and XhoI, was treated with Klenow fragment to generate blunt ends and cloned into the PvuII site of pIng 14.1 (from S. Inglis, Cantab Pharmaceuticals; see also, Digard et al., *J. Biol. Chem.* 265:17393 (1990). The PvuII sites in pIng 14.1 are flanked by a BglII site at one end and a HindIII site at the other end. The resulting plasmid was digested with BglII and HindIII, and the 2.25 kb BglII-HindIII fragment was then inserted between the BamHI and HindIII sites of pMAL-cRI (New England Biolabs) to generate pMAL97 (see FIG. 1). The UL97 gene was thereby placed downstream of and in-frame with a gene encoding maltose-binding protein (MBP), under the control of the IPTG-inducible tac promoter. Transformed bacteria containing pMAL97 were grown in LB medium to an $A_{260}$ of 0.4 mg/ml, and induced with 0.1 mM IPTG at 30° C. for six hours, allowing high-level expression of a 124 Kd MBP-UL97 fusion protein. The resulting MBP-UL97 could be expressed at approximately 2 mg/l following IPTG induction at 30° C., with approximately 40% of the protein remaining soluble. After chromatography on an amylose column, the fusion protein was the predominant species, with three or four minor species.

Preparation of antibodies

MBP-UL97 fusion protein was purified and used to generate antiserum. Protein purification was carried out in the following manner. *E. coli* cells (500 ml culture) that had been transformed with pMAL97 and induced to express MBPUL97 were pelleted, and the cell paste was resuspended in lysis buffer A (20 mM Tris pH 7.4, 0.2 M NaCl, 1 mM EDTA, 1 mM DTT, 1 mM phenylmethylsulfonylfluoride (PMSF), 10% glycerol). The cells were lysed by sonication, and insoluble material was removed by centrifugation. The supernatant was loaded onto an amylose column (New England Biolabs), followed by washing with 5 column volumes of lysis buffer A. The MBP-UL97 fusion protein was eluted with 10 mM maltose in lysis buffer A.

Antiserum against the purified MBP-UL97 fusion protein was prepared by Promega (Madison, Wis.). Rabbits were initially immunized with approximately 500 μg of antigen in 0.5 ml PBS emulsified in 0.5 ml complete Freund's adjuvant. The animals were boosted four times. Boosts were performed using incomplete Freund's adjuvant. Final antisera were collected on day 139.

Construction of recombinant baculoviruses

Recombinant baculoviruses containing the UL97 gene were constructed in the following manner. For each recombinant baculovirus, a transfer plasmid was constructed and then co-transfected with linearized AcNPV DNA (InVitrogen or Pharmingen) using cationic liposomes (InVitrogen) or calcium phosphate. Relevant features of the constructs are shown in FIG. 1. To construct BVUL97, which expresses wild-type UL97, the 2.25 kb MstII-XhoI fragment from pADEH, which contains the AD169 UL97 gene, was treated with Klenow fragment to generate blunt ends. The blunt-ended fragment was ligated with 5'-phosphorylated XbaI linkers and inserted into the NheI site of pBlueBac (Invitrogen) to create transfer plasmid pBlueBac97. In order to construct BVUL97de, which contains the UL97 gene from GCV$^r$ mutant 759rD100, contained within plasmid pGEH7 (described in Sullivan et al., *Nature* 358:162–164 (1992)), was used. This mutant contains a four codon deletion in a conserved region of UL97; in cAMP-dependent protein kinases, this region is involved in substrate recognition. The 2.25 kb MstII-XhoI fragment from pGEH7 was treated with Klenow fragment to create blunt ends. The blunt-ended fragment was ligated with phosphorylated XbaI linkers, and inserted into pBlueBac to create transfer plasmid pBlueBac97de. A recombinant baculovirus, BVUL97K355Q, containing UL97 with the K355Q mutation, was also constructed. In order to create BVUL97K355Q, in which codon 355 of UL97 is altered to specify glutamine rather than lysine, the XbaI fragment of UL97 from pBlueBac9 was cloned into M13mp18 (source). Single-stranded DNA was prepared and used as template for oligonucleotide-directed mutagenesis using an oligonucleotide with the sequence 5' CGCGTGGTCCAGGTG-GCGCG3' [SEQ ID NO:1] according to the method of Taylor et al., *Nucleic Acids Research* 13:8765–8785 (1985) with an in vitro mutagenesis kit (Amersham) according to the manufacturer's instructions. The presence of the K355Q mutation was confirmed by DNA sequencing. The XbaI fragment containing the mutation was inserted into pBlueBac to produce transfer plasmid pBlueBac97K355Q.

An expression vector, BVGSTUL97, containing a gene encoding glutathione-S-transferase (GST)-UL97 fusion protein was also constructed. In order to create BVGSTUL97, plasmid pMAL97 was digested with HindIII and EcoRI, blunt-ended with Klenow fragment, and ligated with a phosphorylated oligonucleotide having the sequence 5'TTTGTTGAAGAATTCTCAACAAA3'[SEQ ID NO: 2], to adjust the ORF and to create EcoRI sites. The ligation product was digested with EcoRI and inserted into the EcoRI site of the pAcG3X baculovirus expression vector (PharMingen) to generate transfer plasmid pGST-UL97. To construct a baculovirus expressing a GSTUL97 fusion protein with the K355Q mutation (BVGSTUL97K355Q), the EcoRI fragment of pGSTUL97 was subcloned into pGEX2T (Pharmacia), resulting in pGEX97. The SphI-PpuMI fragment from the UL97 coding region of pGEX97 was replaced with the corresponding fragment of pBlueBac97K355Q, to create plasmid pGEX97K355Q. The EcoRI fragment of this plasmid was then inserted back into pAcG3X to generate pGST-UL97-K355Q. The orientation of the insert was confirmed by restriction enzyme analysis, and the presence of the K355Q mutation was confirmed by DNA sequencing. To construct BVGST, pAcG3X (Pharmingen), which encodes GST, was used as the transfer plasmid.

Constructs in which the N-terminal region of UL97 was truncated were also made. Oligonucleotides (5'CGAGGATCCCCGCATGCGTTCGA3' [SEQ ID NO:3] for pGST97ΔN103, 5'CCGGATCCCGGGCCCGGGC-CGC3' [SEQ ID NO: 4] for pGST97ΔN238, and 5'CGG-GATCCGCGAGCTCTCTATC3' [SEQ ID NO:5] for pGST97ΔN303) were used to amplify the corresponding fragments by polymerase chain reaction (PCR), using BamHI-linearized pGST97 as template and oligonucleotide 5'ATCGTCAGTCAGTCACGA3' [SEQ ID NO: 6] as the reverse primer. The PCR fragments were cut with BamHI and EcoRI, and inserted into pAcG3X. The SphI-EcoRI, ApaI-EcoRI and SstI-EcoRI fragments were replaced with those of wild type to remove any potential mutation from PCR. The orientation of the inserts downstream from the polyhedrin promoter in these constructs was confirmed by restriction enzyme analysis, and ORF sequences were verified by sequencing.

The recombinant viruses were plaque-purified three times and expanded into virus stocks. Protein expression was confirmed by immunoblotting analysis using antibodies against either GST (Pharmacia) or MBP-UL97 fusion protein. Virus titers were determined and multiplicity of infection (moi) of each virus was adjusted to obtain optimal expression in *Sf*21. Infections were routinely conducted for 46 hrs. Cell lysates from each infection were immunoblotted with anti-MBP-UL97 sera to verify protein expression.

Purification of GST-UL97 fusion protein

All purification steps were performed at 4° C. unless otherwise specified. *Sf*21 cells were infected with BVG-STUL97 or BVGSTUL97K355Q at a moi of 5 pfu/cell at 27° C. At 40 to 46 hrs post-infection, the cells were harvested by scraping and centrifuged at 500 xg for 5 min, and stored as a slurry at −80° C. The cell paste was thawed in 3 volumes lysis buffer D (1×PBS, 10 mM EDTA, 2 mM DTT, 10% glycerol, 1 mM PMSF, 1 mM benzamidine, 0.5 μg/ml leupeptin, 20 μg/ml aprotinin, 1 mM sodium metasulfite, 25 μg/ml antipain, 10 μg/ml pepstatin A and 7 μg/ml E-64; protease inhibitors were obtained from Sigma).

Cell lysis was achieved by French press at 1000 psi. A crude extract was prepared by centrifuging the homogenate at 10,000×g for 30 min. The resulting supernatant was loaded on a 3 ml glutathione affinity column (Pharmacia). The column was washed with 20 ml lysis buffer D and protein was eluted with elution buffer (50 mM Tris pH 8.0, 10% glycerol, 2 mM EDTA, 2 mM DTT, 50 mM NaCl, 10 mM reduced glutathione). Fractions containing GST fusion proteins were pooled and applied to a Q-Sepharose fast flow column (Pharmacia), and eluted using a 0.2–1.0 M NaCl gradient in elution buffer. The GST fusion proteins were pooled and repurified using a glutathione column to remove NaCl, and subjected to chromatography on a SP Sepharose high performance column (Pharmacia) using a 0.1–10 M NaCl gradient in elution buffer. Fractions containing GST-UL97 were collected and concentrated by Centricon 30 (Amicon). Protein concentrations were determined by a microassay system (Bio-Rad) using bovine serum albumin as a protein standard, and a predicted molecular mass of 104 Kd for GST-UL97. Purified protein preparations were stored at −80° C.

Partial purification of full length UL97

All operations were performed at 0–4° C. unless otherwise specified. Sf9 cells were infected with either BVUL97 at a moi of 5 and incubated at 27° C. for 40–46 hrs. Infected cells were scraped into the culture medium, centrifuged for 5 min at 800×g, washed with cold phosphate buffered saline (PBS) and resuspended in 50 mM Tris HCl pH 8.0, 10 mM $MgCl_2$ 0.5% Nonidet P-40 (NP-40), 1 mM PMSF, 1 mM benzamidine, and 2 mM DTT (lysis buffer C). The cells were incubated for 10 min and then sheared by six strokes in a Dounce homogenizer. The nuclei were collected by centrifugation for 5 min at 1800×g, resuspended in Buffer A, frozen on dry ice, and stored at −80° C. The nuclei were subsequently thawed on ice, and 5M NaCl was added to a final concentration of 0.6M. The samples were gently rocked for 40 min, and then DNase I was added to 0.1 mg/ml. Following another 40 min. incubation, the samples were centrifuged for 5 min at 10,000 ×g. The pellet was resuspended in lysis buffer C containing 10% glycerol and stored at −80° C. The material was thawed for use in the protein kinase assay.

Determination of UL97 consensus phosphorylation sequences

The optimal sites for phosphorylation by UL97 protein kinase are determined as described previously. Songyang et al., *Current Biology* 4:973–982 (1994). Briefly, oriented libraries containing peptide substrates are generated. The consensus sequences of optimal substrates are determined by sequencing the mixture of products generated during a reaction with UL97 protein kinase.

Preparation of peptides containing UL97 consensus phosphorylation sequences

GST-UL97 was phosphorylated in vitro. The radiolabelled protein was then digested with trypsin, and peptides were resolved by high performance liquid chromatography (HPLC) on a C-18 reversed phase column. Individual radioactive peaks were further purified using the same column and subjected to automated protein sequencing.

Immunochemistry

For immunoprecipitation, cells were sonicated in 1 ml ice-cold immunoprecipitation (IP) buffer (50 mM Tris HCl pH 7.6, 100 mM NaCl, 5 mM $MgCl_2$, 0.1% NP-40, 10% glycerol, 10 mg/ml aprotinin, 10 mg/ml leupeptin and 1 mM PMSF), and insoluble material was removed by centrifugation at 12,000×g for 5 min. Anti-MBP-UL97 sera (2 μl) was added to the supernatant. The immunoconjugates were adsorbed with 50 μl of 10% (w/v) Protein A-Sepharose 4B (Sigma) at 4° C. on a rocking platform, centrifuged at 12,000×g for 1 min and washed twice with IP buffer. Adsorbed immunocomplexes were resuspended in 1× Laemmli sample buffer (62.5 mM Tris HCl pH 6.8, 10% glycerol, 100 mM DTT, 1% SDS, 0.001% bromophenol blue) and boiled for 2 min.

For Western blotting, proteins were separated on 10% SDS-PAGE gels and electrophorectically transferred to nitrocellulose membranes (Schleicher & Schuell). After transfer the membranes were incubated for thirty min in 3% nonfat dry milk (Bio-Rad) in TTBS buffer (20 mM Tris pH 7.5, 0.9% NaCl, 0.1% Tween 20) followed by washing with TTBS buffer. The membranes were then incubated for 30 min at room temperature with primary antibodies diluted 1:300 in TTBS buffer, followed by incubation with alkaline phosphate-conjugated anti-rabbit antibodies in TTBS buffer for 30 min. Immunoreactive bands were detected using 5-bromo-4-cholo-3-indolylphosphate (0.15 mg/ml) and nitro blue tetrazolium (0.3 mg/ml) in 50 mM Tris pH 9.5, 5 mM $MgCl_2$.

To assay relative UL97 concentrations in cell extracts, Western blots were made from gels containing dilutions of each sample and dilutions of known amounts of UL97 were developed as above, using conditions under which the intensities of the UL97 signals obtained were proportional to the amount of UL97 loaded on the gel ($R \geq 0.89$). The blots were scanned using a Microtek scanner, a MacIntosh computer and Adobe Photoshop. The intensities of the UL97 bonds were measured using Image 1.31 p, and compared with a standard curve based on the known amounts of UL97 loaded on the gel.

Anabolism of DHPG

*Sf*9 monolayers in 35 mm diameter dishes were infected at a moi of 0.2 pfu/cell. At three days post-infection, the cells were pulse-labeled with 50 μM $^{14}$C-labeled DHPG (specific activity, 52 mCi/mmol) which had been purified by HPLC to remove guanine contaminants. Cells were extracted with perchloric acid, and DHPG anabolites were determined with a cation-exchange column as described previously (Stanat et al., *Antimicrob. Agents Chemother.* 35:2191–2197 (1991)).

Identification of phosphoaminoacids

Partially purified proteins were obtained as described above. After in vitro phosphorylation, phosphoproteins were resolved by electrophoresis on 10% SDS-PAGE gels. The portion of the gel containing UL97 was excised and ground into small pieces. Radioactive peptide, eluted by boiling for 3 min in 50 mM ammonium bicarbonate, 10 mM β-mercaptoethanol and 0.3% SDS, was co-precipitated with 20 μg BSA in ice-cold 20% trichloroacetic acid. The pellet was washed with ethanol, dried and then subjected to acid hydrolysis in 6 N HCl (50 μl) for 3 hrs at 110° C. After drying, the samples were spotted onto a cellulose thin layer plate with a mixture of unlabelled phosphoserine, phosphothreonine, and phosphotyrosine and subjected to electrophoresis at pH 1.9 (acetic acid:formic acid:water, 78:25:897) in one dimension and at pH 3.5 (butanol:pyridine:acetic acid:water, 15:10:3:127) in the other dimension. The plate was then stained with ninhydrin to locate the positions of the unlabelled phosphopeptides, and autoradiographed.

Protein kinase assay

Protein samples were added to 20 μl of reaction buffer containing 50 mM Tris HCl pH 9.0, 10 mM $MgCl_2$, 5 μM ATP, 2 mM DTT, 1 M NaCl and 5 μCi $\gamma^{32}$P-ATP (unless otherwise stated). After incubation at 37° C. for 30 min (unless otherwise stated), the reactions were terminated by addition of 20 μl of 2× Laemmli sample buffer to the sample and boiling for 3 min. Phosphorylated proteins were resolved by electrophoresis on 10% SDS-PAGE gels and detected by autoradiography. In order to quantitate the level of phosphorylation, the region of the gel corresponding to the labelled protein was excised and the Cerenkov radioactivity was counted. For assay of extracts of insect cells infected with BVUL97 and related recombinant viruses, $2 \times 10^7$ infected or mock-infected cells were broken by sonication in 1 ml of ice-cold lysis buffer B (50 mM Tris-HCl pH 7.6, 100 mM NaCl, 5 mM $MgCl_2$, 0.1% NP-40, 10% glycerol, 10 mg/ml aprotinin, 10 mg/ml leupeptin and 1 mM PMSF). Insoluble material was removed by centrifugation at 12,000×g for 5 minutes.

In order to determine the stoichiometry of autophosphorylation, the reaction was carried out as above, except that incubation was for 120 min. In another method used to quantitate the extent of autophosphorylation, unincorporated $\gamma^{32}P$-ATP was removed with a Microcon 10 (Amicon) by dilution-concentration cycles with a negative control without GST-UL97. The remaining radioactivity on the Microcon membrane was counted in 10 ml scintillation fluid (Packard). A counts per minute to picomole conversion factor was determined for each assay and used to calculate picomoles of ATP by comparing to the manufacturer's specification of $\gamma^{32}P$-ATP concentration to the actual counts/minute measured.

Assay to Detect UL97 Substrates

Potential UL97 substrates were dissolved in reaction buffer and UL97 protein was added. For example, 0.8 µg/µl of a histone preparation was dissolved in 20 µl reaction buffer, and 1.9 ng/µl GST-UL97 was added. Following a 30 min incubation at 37° C., reactions were terminated by the addition of 2×Laemmli sample buffer, and the samples were boiled for 3 min. Proteins were separated on 15% SDS-PAGE gels, and phosphorylation of substrates was detected by autoradiography.

Assay to detect inhibitors or activators of UL97 protein kinase activity

Exogenous UL97 substrates identified in the substrate assay are used to detect agents which affect UL97 protein kinase activity. For example, Histone (Type II AS, Sigma) which was identified by the substrate assay, was used without further purification as an exogenous substrate for UL97 phosphorylation. In a typical reaction, 0.8 µg/µl histone was dissolved in 20 µl reaction buffer, and the reaction was initiated by addition of 1.9 ng/µl GST-UL97. Following a 30 min incubation at 37° C., the reaction was terminated by the addition of 2× Laemmli sample buffer to the sample and boiling for 3 min. Proteins were separated on 15% SDS-PAGE gels, and phosphorylation was detected by autoradiography.

Results

Figure 2:
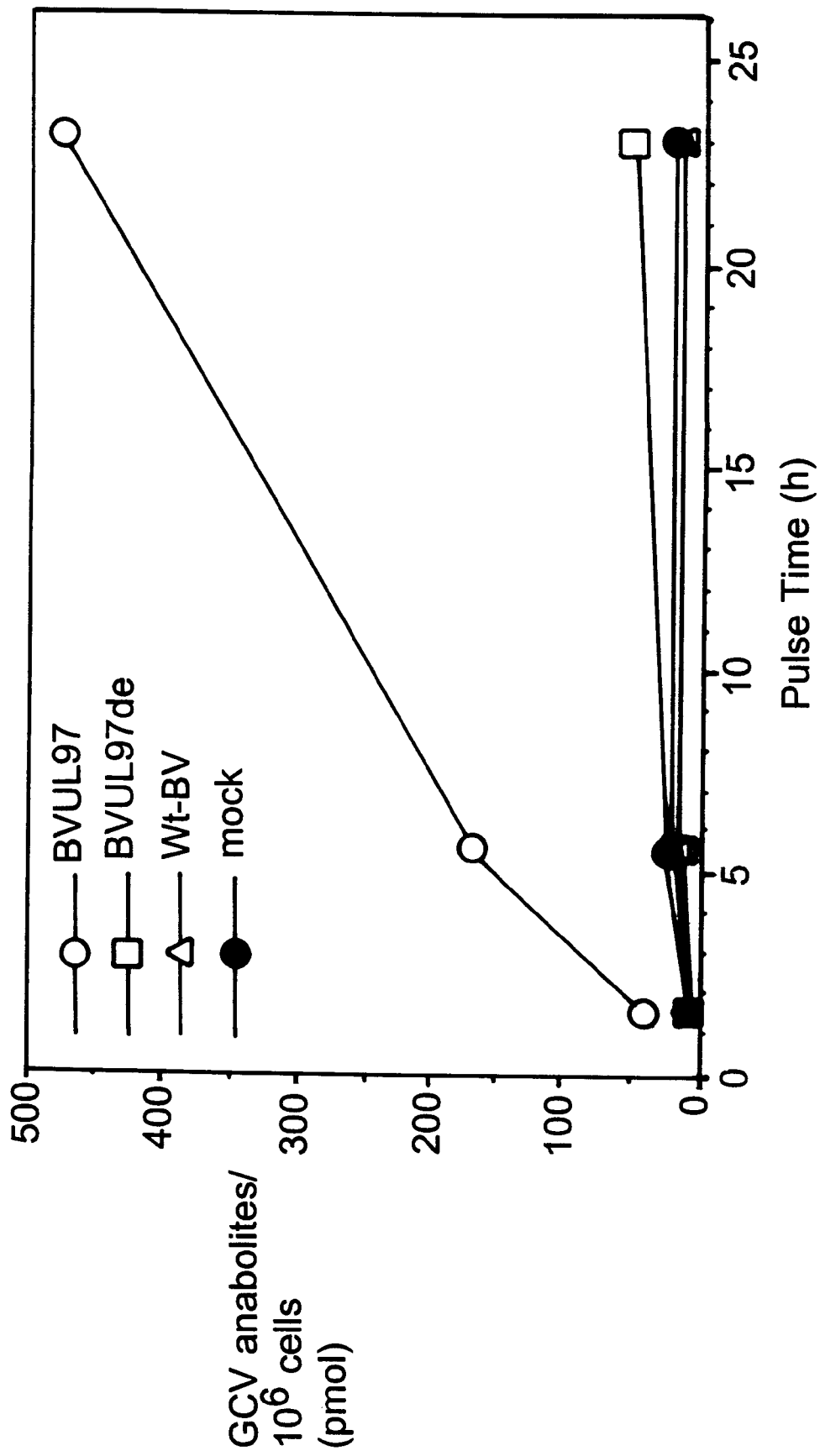
FIG. 2 is a graph showing induction of GCV phosphorylation in insect cells by BVUL97.

Induction of GCV phosphorylation by UL97 in recombinant baculovirus-infected insect cells The recombinant baculovirus system was used to express enzymatically active UL97. The wild type UL97 gene from CMV strain AD169, and the UL97 gene containing a four codon deletion (Δ590–593) from the mutant 759rD100, which confers GCV resistance (Sullivan et al., Nature 358:162–164 (1992); corrections in 359:85 and 366:756), were each introduced into baculovirus under the control of the polyhedrin promoter. The resulting viruses, BVUL97 and BVUL97de (FIG. 1), express a new polypeptide of approximately 80 Kd that reacts with anti-UL97 antisera on Western blots. To determine if the expressed UL-97 was biologically active, the anabolism of radiolabelled GCV in mock-infected insect cells or insect cells infected with either BVUL97, BVUL97de, or baculovirus containing no insert (wt-BV) was measured. Radiolabelled GCV anabolites were measured following cation-exchange chromatography. The results are shown in FIG. 2. BVUL97-infected cells phosphorylated GCV far more effectively than did cells infected with wild type BV or mock-infected cells. The rate of phosphorylation in the BVUL97-infected insect cells was similar to that observed in CMV-infected human cells. See, e.g., Sullivan et al., supra. BVUL97de was severely impaired for induction of GCV phosphorylation. Thus, baculovirus-expressed UL97 is biologically active, as measured by GCV phosphorylation, and the four codon deletion that impairs GCV phosphorylation in CMV-infected cells exerts the same effect in insect cells.

Phosphorylation of baculovirus-expressed UL97

To determine whether UL97 was capable of autophosphorylation, cell extracts were reacted with antiserum to UL97, and the immunoprecipitates were tested for the ability to phosphorylate UL97. Extracts of either BVUL97 or CMV-infected HFF cells were incubated with UL97 antiserum, and the immunoconjugates were collected with protein A-Sepharose and incubated with $\gamma^{32}P$-ATP. An 80 Kd polypeptide was the major labelled species. No labelling was observed when extracts of mock-infected HFF cells or wt-BV-infected insect cells were subjected to immunoprecipitation and incubation with $\gamma^{32}P$-ATP. The 80 Kd species detected by immunoprecipitation comigrated with BVUL97-expressed UL97 detected by Coomassie staining or Western blot analysis.

In other experiments, extracts of insect cells infected with BVUL97 were incubated with $\gamma^{32}P$-ATP. Under the conditions used (high salt and high pH), which suppress endogenous kinase activities, an 80 Kd polypeptide was the major labelled species. This labelled species comigrated with BVUL97-expressed UL97 detected by Coomassie staining or Western blot analysis. No labelling at this position was observed when extracts of mock-infected HFF cells or wt-BV-infected insect cells were subjected to incubation with $\gamma^{32}P$-ATP.

Figure 3A:
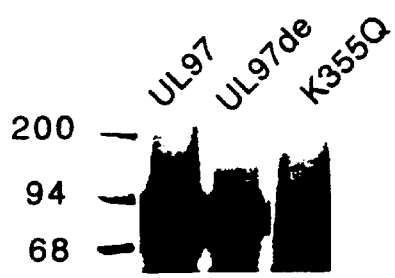
FIG. 3 is an autoradiograph (A) and a Western blot (B) of phosphorylated baculovirus-expressed UL97.
Figure 3B:
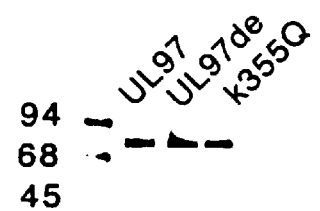

To examine the apparent UL97 autophosphorylation further, mutant forms of UL97 were tested for this activity. Insect cells were infected with either BVUL97, BVUL97de, or BVUL97K355Q (FIG. 1). The latter mutant contains a glutamine in place of lysine that corresponds to an invariant lysine in subdomain II of protein kinase; this lysine cannot be mutated without loss of activity. Hanks et al., Science 241:42–52 (1988). In cAMP-dependent protein kinase, this lysine aligns with the phosphates of ATP. Knighton et al., Science 253:407–414 (1991). Extracts were prepared and incubated with $\gamma^{32}P$-ATP under conditions of high salt and high pH that had been preliminarily shown to be optimal for UL97 phosphorylation, and which suppress endogenous kinase activities. In these experiments, equal aliquots of each extract were subjected to SDS-polyacrylamide gel electrophoresis. Gels were then either subjected to autoradiography (FIG. 3, Panel A) or Western blot analysis (FIG. 3, Panel B). The leftmost lane in each panel contains protein size markers and the sizes of the proteins are indicated to the left of the panels. As shown in FIG. 3, substantial labelling of UL97 was observed in extracts of BVUL97 and BVULde-infected cells. Little or no labelling of UL97 was observed in extracts of BVUL97K355Q-infected cells or in mock-infected cells, although the extract contained a similar amount of UL97 as did the other extracts (FIG. 3). The amounts of UL97 present in the various cell extracts was compared by semi-quantitative Western blot analysis (see Materials and Methods) and the relative amount of labelling per UL97 protein of various mutants was determined. The K355Q point mutant was impaired 20-fold or more in its ability to phosphorylate. This finding strongly suggests that UL97 catalytic activity is required for UL97 phosphorylation. However, the four codon deletion in BVUL97de, which severely impairs GCV phosphorylation, had only a 2- to 3-fold effect on UL97 phosphorylation (44% of the specific activity of BVUL97).

UL97 becomes phosphorylated on serine and threonine

Figure 4:
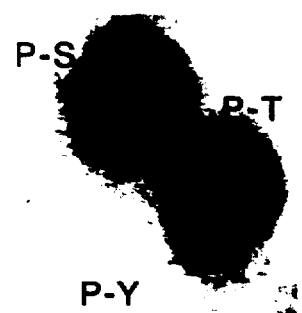
FIG. 4 is an autoradiograph showing phosphoamino acid analysis of baculovirus-expressed UL97.

In order to determine which amino acids were autophosphorylated in UL97, UL97 was partially purified from BVUL97-infected cells. The partially purified UL97 was incubated in vitro with $\gamma^{32}$P-ATP, and the labelled UL97 was purified by electrophoresis, acid-hydrolyzed, and mixed with unlabeled phosphoamino acids. The mixture was then subjected to two-dimensional electrophoresis, and the thin-layer plate was visualized with ninhydrin and autoradiographed. A typical autoradiograph is shown in FIG. 4. The positions of unlabelled phosphoserine (P-S), phosphothreonine (P-T), and phosphotyrosine (PY) are indicated. Approximately 65% of the radioactivity detected co-migrated with phosphoserine and about 35% with phosphothreonine. No labelled species corresponding to phosphotyrosine was observed. Thus, the protein kinase associated with UL97 is a serine/threonine kinase.

The serine/threonine specificity of UL97 is of interest, in part because of the lack of conservation of UL97 with other protein kinases in subdomains VI and VIII (FIG. 1), which correspond to the catalytic and P+1 loops in protein kinase structures, respectively, and which are implicated in recognition of the correct hydroxyamino acid (Hanks et al., *Science* 241:42–52 (1988); Hubbard et al., *Nature* 372:746–754 (1994); Knighton et al., *Science* 253:407–414 (1991). The sequence of subdomain VI in UL97 is $^{456}$Asp-Ile-Thr-Pro-Met-Asn [SEQ ID NO:7], where Asp-456 corresponds to the catalytic Asp in cAMP-dependent protein kinase. Pro-459 corresponds to prolines that are found in many serine/threonine kinases, but which are very unusual in tyrosine kinases. Hanks et al., supra. The consensus sequence of subdomain VIII for serine/threonine kinases is Gly-Thr/Ser-X-X-Tyr/Phe-X-Ala-Pro-Glu [SEQ ID NO:8], (where "X" is defined as any amino acid) (Id.), with an important role for an interaction of the thr/ser residue with the catalytic loop in hydroxyamino acid selection. Knighton et al., supra. Subdomain VIII is difficult to locate in UL97 (Chee et al., *J. Gen. Virol.* 70:1151–1160 (1989)), but an alignment with its homologs in other herpesviruses suggests that its sequence is $^{517}$Tyr-His-Pro-Ala-Phe-Arg-Pro-Met-Pro [SEQ ID NO:9] (dewind et al., *J. Virol.* 66:200–5209 (1990)), with only Phe-521 conserved with conventional serine-threonine kinases. Both Pro-459 and Phe-521 are adjacent to residues that, when mutated, confer GCV-resistance, consistent with a role in substrate selection.

Production of a soluble, enzymatically active UL97 fusion protein

Although relatively high levels of UL97 could be expressed using BVUL97, and the data indicated that at least some of the this protein was active, the expression system suffered from a number of drawbacks. First, the extent of phosphorylation was less than 1%, suggesting that a large proportion of the protein was not active. Secondly, the vast majority of the protein behaved as if it were insoluble, co-sedimenting with nuclei following cell lysis and sedimenting at low speed even after the nuclei were lysed with high salt and treated with DNase. Interestingly, this material did not have a specific activity which was meaningfully lower than the material that did not sediment following cell lysis. Thirdly, although the rapid sedimentation of the protein made it easy to obtain UL97 at approximately 80% purity, it was difficult to purify it any further without loss of activity.

Therefore, ways to increase the solubility of UL97 while retaining its activity were sought. For this purpose, UL97 was expressed as a GST-fusion protein using recombinant baculovirus BVGSTUL97 (FIG. 1). A mutant UL97 containing the lysine to glutamine alteration that inactivates UL97 phosphorylation activity, expressed from recombinant baculovirus BVGSTUL97K355Q, as well as GST alone, expressed from the recombinant baculovirus BVGST, were used as controls. *Spodoptera frugiperda* cells were infected with the recombinant viruses, and 40–46 hrs later the cells were lysed. Immunoblotting using polyclonal antiserum to the MBP-UL97 fusion protein, which recognizes the UL97 portion of the GST-UL97 fusion protein, revealed an immunoreactive band of approximately 104 Kd in cells infected with the recombinant viruses. This band was not detected in cells infected with wild type baculovirus. The 104 Kd band corresponded with a protein band visualized with Coomassie blue at approximately 104 Kd in cells infected with the recombinant viruses, but not in cells infected with wild type baculovirus.

Figure 5:
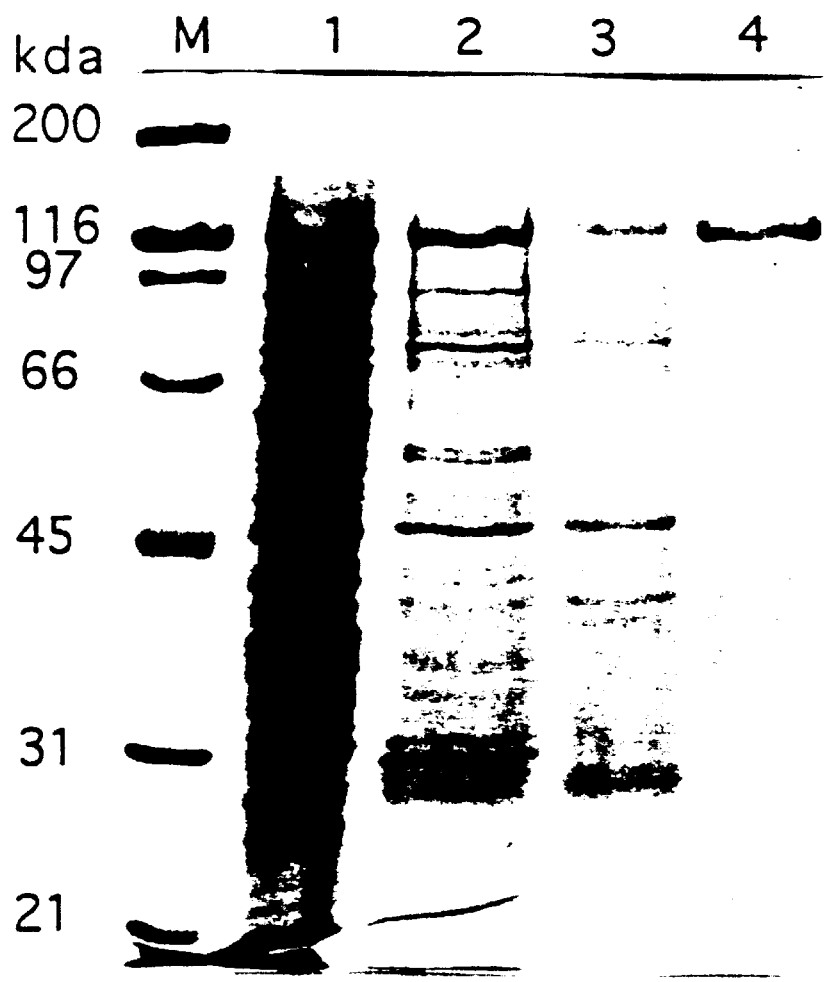
FIG. 5 is a Coomassie-blue stained SDS gel showing GST-UL97 at various stages of purification.

GST and both the wild type and mutant fusion proteins were expressed to high levels as species of the expected sizes that reacted with anti-UL97 and/or anti-GST sera on Western blots. The fusion proteins could be readily purified to apparent homogeneity using glutathione sepharose, Q-sepharose and SP Sepharose, while GST was purified to apparent homogeneity simply by using glutathione-sepharose. FIG. 5 shows a Coomassie-blue stained SDS polyacrylamide gel of aliquots of protein markers (lane M), lysate of insect cells infected with BVGSTUL97 (lane 1), eluate of a glutathione affinity column of the lysate (lane 2), pooled fractions from Q-sepharose chromatography (lane 3), and concentrated fractions from SP sepharose chromatography (lane 4). The sizes of protein markers in Kd are indicated to the left in the figure.

Approximately 50% of the fusion protein purified on the GST-Sepharose affinity column was full length (FIG. 5, lane 2). A major species migrating at approximately 26 Kd most likely represents degradation products of the full length GST-UL97 fusion proteins, since purification of free GST under identical conditions yielded virtually homogeneous protein, and the 26 Kd species cross-reacted with anti-GST serum. The amount of degradation product increased as the infection progressed, indicating that these products are generated in vivo. Protease inhibitors were added to the lysis buffer to prevent in vitro degradation from occurring. After chromatography on the GST affinity column, no significant degradation of GST-UL97 proteins was observed.

Since analysis of the UL97 primary structure predicted an isoelectric point of 7.35, and initial experiments showed that free GST does not bind to Q-Sepharose high performance at pH 8.0, the proteins were further chromatographed on a Q-Sepharose column to remove GST-containing degradation products (FIG. 5, lane 3). GST-UL97 proteins which bound strongly to the column were then eluted at approximately 0.5M NaCl. Active fractions were pooled, desalted on a glutathione-Sepharose 4B column, and applied to a SP Sepharose column (FIG. 5, lane 4). Analysis of the purified proteins on SDS-PAGE gels showed a single band which was at least 95% pure.

Figure 6:
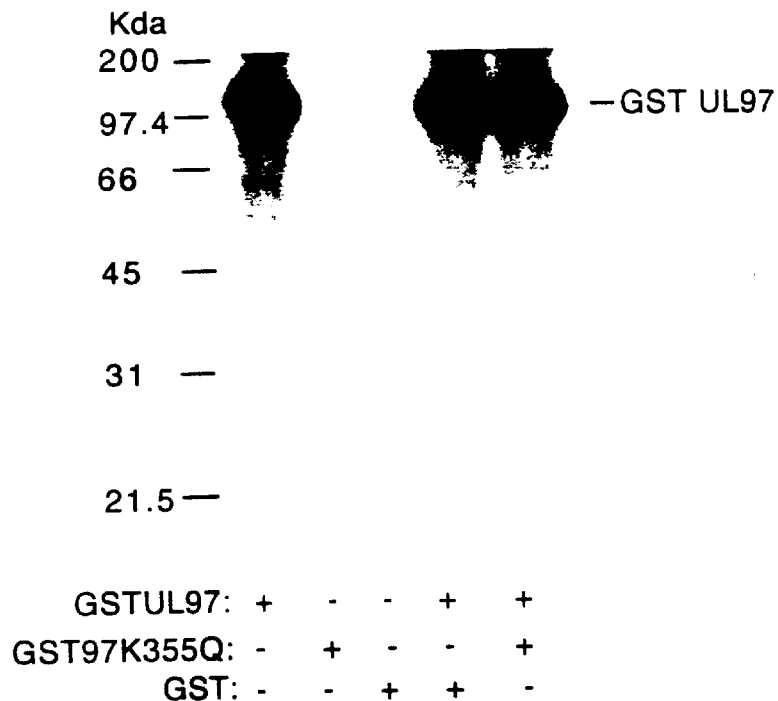
FIG. 6 is an autoradiograph showing phosphorylated GST-UL97.

When equal amounts of purified GST, GSTUL97, or GSTUL97K355Q were incubated with $\gamma^{32}$P-ATP, only the wild type fusion protein became labelled. FIG. 6 shows an autoradiograph of a typical gel. The protein content of the mixtures is indicated at the bottom (+, protein present; −, protein absent). The positions of protein of the indicated sizes is provided at the left and the position of GST-UL97 is provided at the right. Autoradiography revealed a single phosphorylated band at approximately 104 Kd, the size of the GST-UL97 fusion protein. This band is the result of autophosphorylation of GST-UL97, since phosphorylation was abolished by a point mutation (the K355Q mutation) in the catalytic domain of UL97. Phosphorylation was on the UL97 portion of the fusion protein, not on the GST portion. The mutant protein preparation did not prevent phosphorylation of the wild-type protein, indicating that its failure to become phosphorylated was not due to a contaminating inhibitor.

In order to determine which regions in GST-UL97 were autophosphorylated, a cleavage site for the protease Factor Xa at the junction of GST and UL97 was utilized. $^{32}$P-labelled GST-UL97 fusion protein was digested with Factor Xa for 18 hrs at 4° C., and the digests were subjected to electrophoresis on 15% SDS-PAGE gels, followed by autoradiography. Radioactive bands larger than 7 Kd were not found, indicating that the labeled GST-UL97 was degraded by Factor Xa. When Factor Xa digests were subjected to SDS-PAGE and Western blot analysis, a 29 Kd band visualized by Coomassie blue was recognized by anti-GST antibody, indicating that the GST region in GST-UL97 was not degraded by Factor Xa and was not labelled. Moreover, the fusion protein was not able to phosphorylate free GST (FIG. 6). Therefore, the phosphorylation sites in the GST-UL97 fusion protein reside in the UL97 region of the protein.

Properties and kinetics of the phosihorylation reaction

Figure 7A:
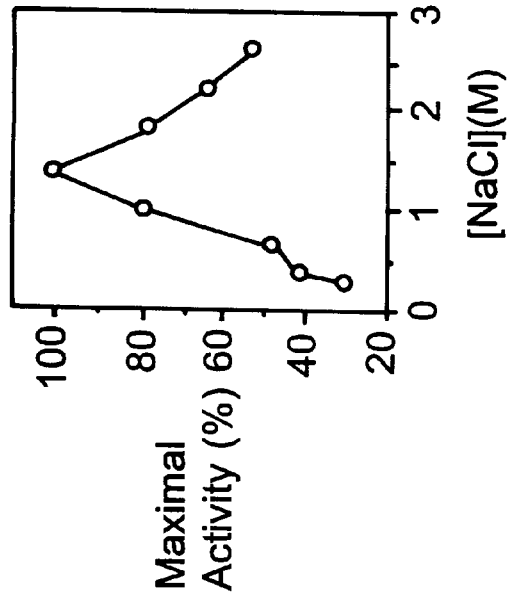
FIGS. 7A, B and C are graphs showing the optimal conditions for GST-UL97 phosphorylation.
Figure 7B:
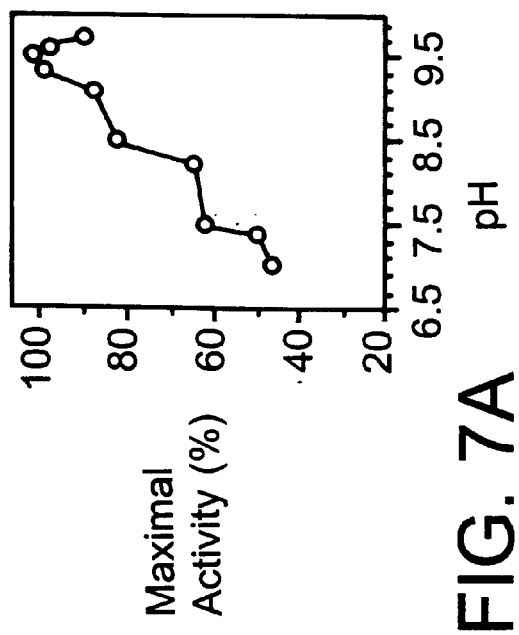
Figure 7C:
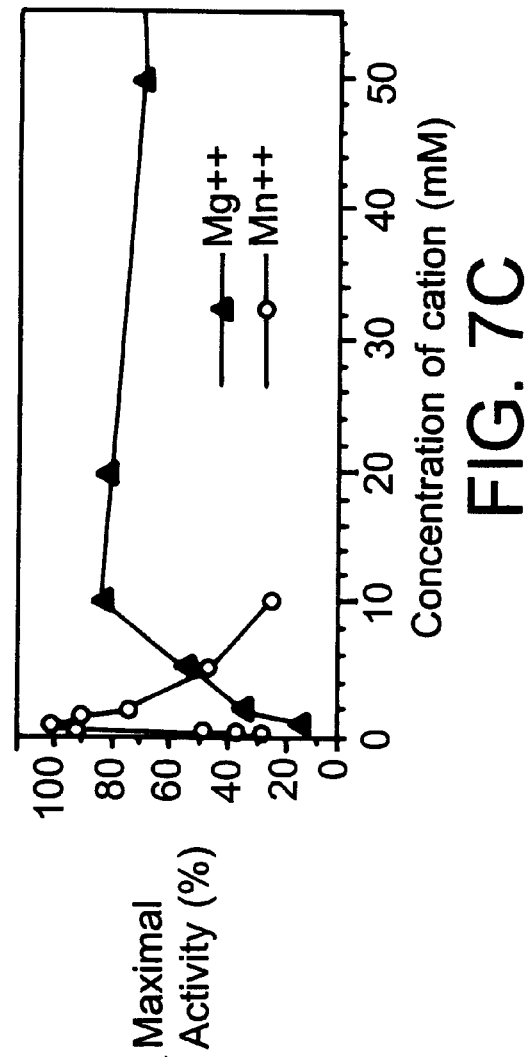

Some characteristics of the phosphorylation reaction are shown in FIG. 7. For these experiments, GST-UL97 was incubated with radiolabelled ATP using standard protein kinases assay conditions (see Materials and Methods) except that the reactions were for one minute (to measure initial rates) and the pH (panel A), NaCl concentration (panel B), and divalent cation concentration (panel C) were varied as indicated. The incorporation of phosphate into GST-UL97 was determined for each condition. As shown in FIG. 7, the activity required divalent cations, with a preference for $Mn^{2+}$ (optional concentration, approximately 1 mM). $Mg^{2+}$ could substitute for $Mn^{2+}$ (optimal concentration, approximately 10 mM), but less activity was observed. Neither $Co^{2+}$, $Ca^{2+}$ nor $Zn^{2+}$ at concentrations between 1 and 10 mM supported phosphorylation. Compared to other protein kinases, such as cAMP-dependent kinase or Pseudorabies virus-encoded kinase (Purves et al., *Eur. J. Biochem.* 167:507–512 (1987)), UL97 is highly resistant to high concentrations of NaCl, with 50% activity retained at 2.8 M NaCl and an optimum NaCl concentration of approximately 1.5 M. Like herpes simplex virus-encoded US3 kinase (Daikoku et al., *Virology* 197:685–694 (1993)), UL97 is active over a broad pH range. Phosphorylation was greatest at high pH, with maximal phosphate incorporation occurring at a pH of 9.0 to 9.5. UL97 is thus distinct from the CMV serine/threonine kinase described by Michelson et al. (*Eur. J. Biochem.* 149:393–399 (1985); *Virology* 134:259–268 (1984), which is not characterized by a high pH optimum or a preference for $Mn^{2+}$.

Figure 8:
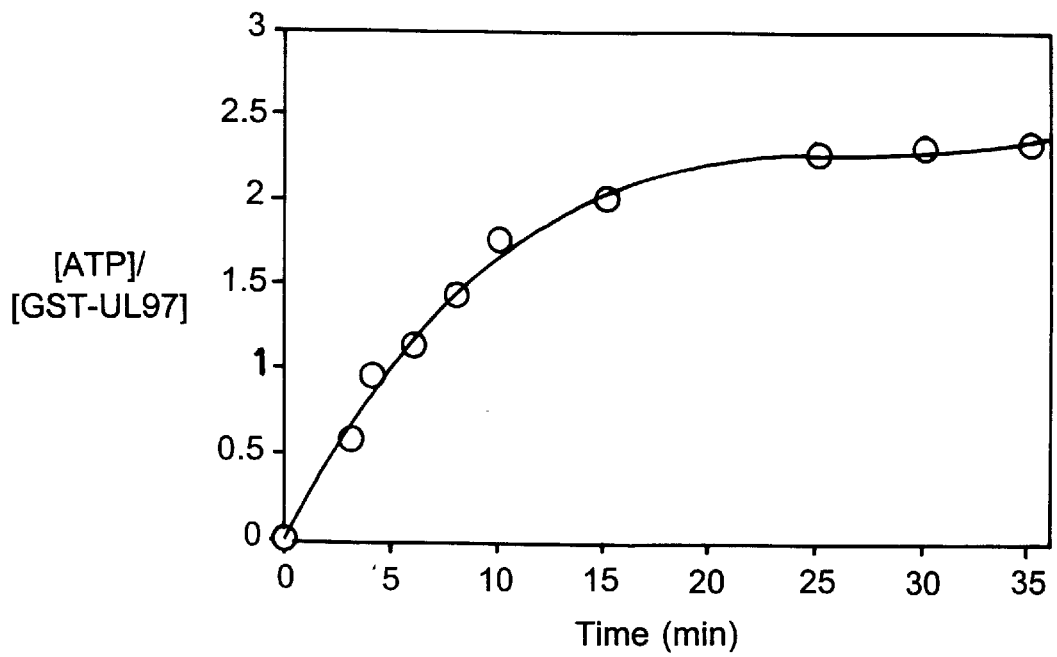
FIG. 8 is a graph showing a time course of phosphate incorporation by GST-UL97.

The Michaelis or apparent dissociation constant ($K_m$) for GST-UL97 was determined using a Lineweaver-Burk plot. Kinase reactions (enzyme concentration, 4.7 ng/µl) were carried out in 200 µl standard assay buffer. Aliquots (15 µl) were removed at the times indicated in FIG. 8, and the reactions were stopped by the addition of 15 µl 2×SDS sample buffer and boiling for 3 min. Radiolabelled GST-UL97 was separated on 10% SDS-PAGE gels and quantified by Cerenkov count. At the optimal divalent cation concentration, the $K_m$ determined for ATP as substrate was 2.0±0.5 µM. GST-UL97 was also able to utilize GTP as a phosphate donor, with a $K_m$ of 4 µM at 10 mM $Mg^{2+}$. Similar results were obtained with BVUL97-expressed UL97. Incorporation of phosphate by purified GST-UL97 was a very rapid process under the assay conditions (FIG. 8), suggesting that an intramolecular process is involved in phosphorylation. Autophosphorylation was linear for approximately 10 min, and the reaction was complete in approximately 25 min. GST-UL97 phosphorylation reached 2.8±0.35 Pi/mol, indicating that three sites in UL97 were phosphorylated.

Figure 9:
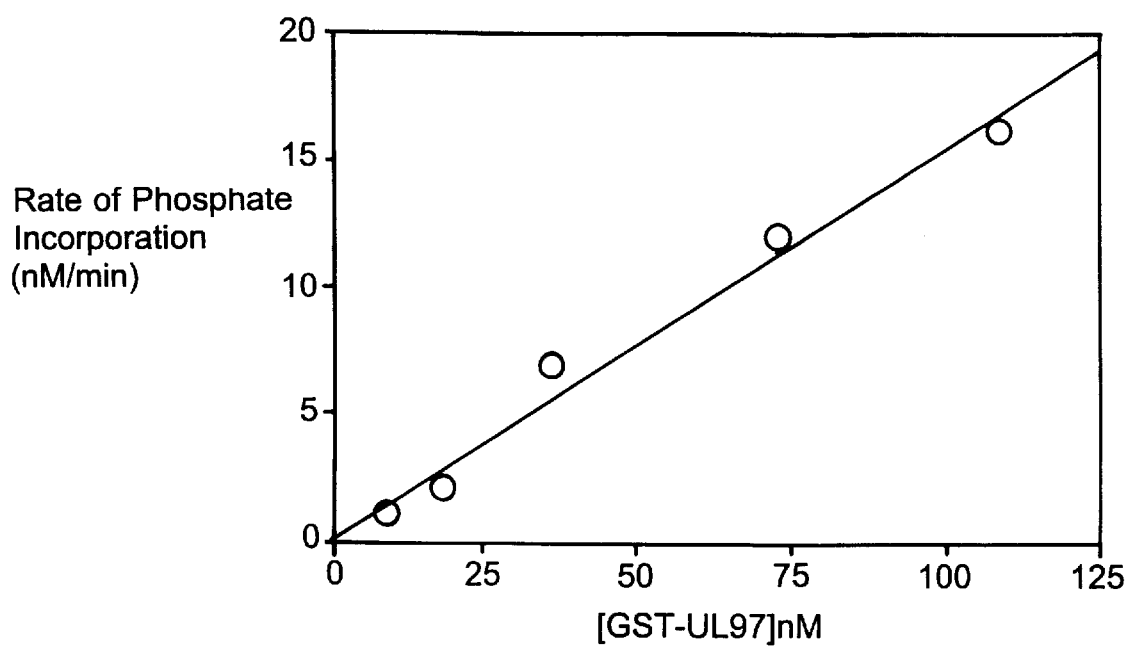
FIG. 9 is a graph showing the rate of autophosphorylation as a function of GST-UL97 concentration.

To confirm that UL97 autophosphorylates, the initial rate of phosphorylation (3 minute reactions) of purified GST-UL97 by different concentrations of protein was also examined (FIG. 9). If UL97 autophosphorylates, then one would expect the rate of phosphorylation to be directly proportional to protein concentration over a wide range of concentrations. If there were a contaminating protein kinase responsible for phosphorylation, then the phosphorylation rate would be expected to increase hyperbolically with protein concentration via second order kinetics, because both the contaminating protein kinase and its substrate, i.e., UL97, would vary coordinately. In these experiments, the reactions were terminated at 3 min by the addition of 2×SDS sample buffer and boiling for 3 min. The data were fit by least squares analysis. When assayed under linear reaction conditions, e.g., for 3 min, the rate of phosphate incorporation was directly proportional to the protein concentration over a wide range (FIG. 9). The reaction followed first order kinetics and had a rate constant of 0.18±0.03 min$^{-1}$, i.e., the rate of incorporation per protein molecule did not vary with protein concentration, indicating that a contaminating protein kinase is not involved in UL97 phosphorylation. These findings support the hypothesis that phosphorylation of UL97 occurs via a intramolecular mechanism and are consistent with UL97 autophosphorylation. This interpretation is consistent with the finding that autophosphorylation was not stimulated by the addition of a 5-fold excess of GST-UL97-K355Q to the wild type enzyme (FIG. 6).

Figure 10A:
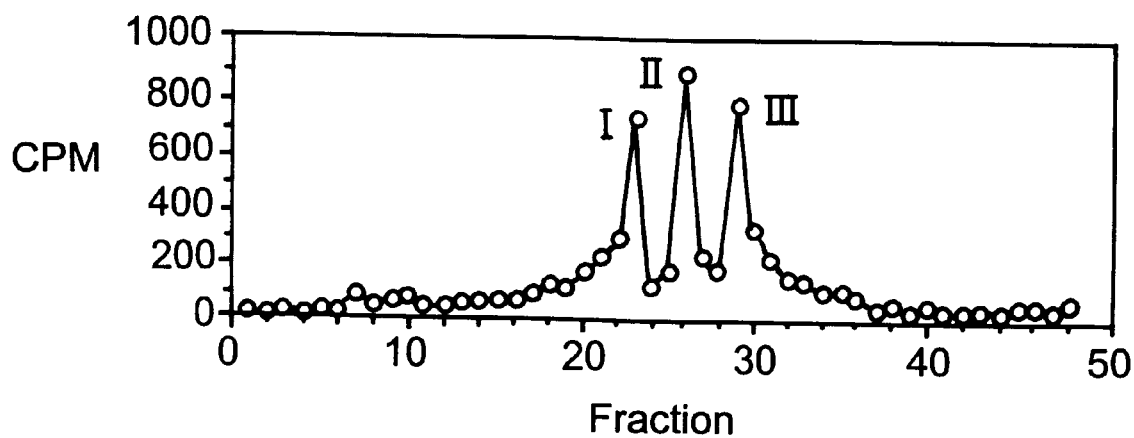
FIGS. 10A, B and C are graphs showing UL97 phosphorylation sites.
Figure 10B:
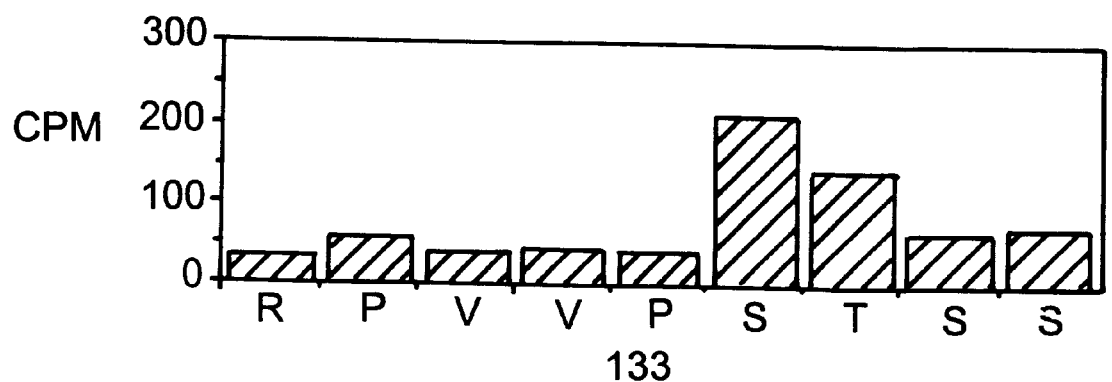
Figure 10C:
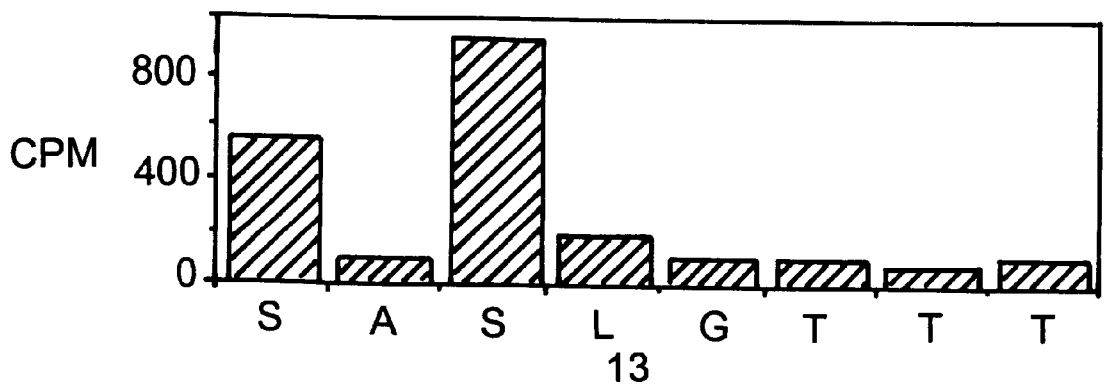

In order to determine the sequences of the phosphorylation sites in UL97, autophosphorylated GST-UL97 was digested with trypsin, and radioactive tryptic peptides were isolated by HPLC. Three peaks were observed and purified (FIG. 10, panel A). Two of these were sequenced by automated peptide sequencing and the fractions were assayed for release of radioactivity. The sequence of the peptides and the corresponding release of radioactivity for these peaks are shown in FIG. 10, panels B and C. The letters under the graphs refer to the standard one letter symbols for amino acids, i.e., R is arginine, P is proline, V is valine, S is serine, T is threonine, A is alanine, L is leucine, and G is glycine. Two autophosphorylation sites were identified, one on Ser-13 and the other on Ser-133. Interestingly, these residues are embedded within serine/threonine rich contexts, which may be indicative of substrate preferences for UL97. Radioactivity was also observed at cycle 134. Mass spectroscopic analysis (performed at the protein chemistry facility at the Dana-Faber Cancer Institute, Boston, Mass.) revealed that the size of the peptide was consistent with only one phosphate, indicating that the radioactivity at this position was due to carryover from Ser-133. The radioactivity in cycle Ser-11 is most likely due to release of unimmobilized radioactive peptide.

Phosphorylation of exogenous substrates by GST-UL97

Figure 11:
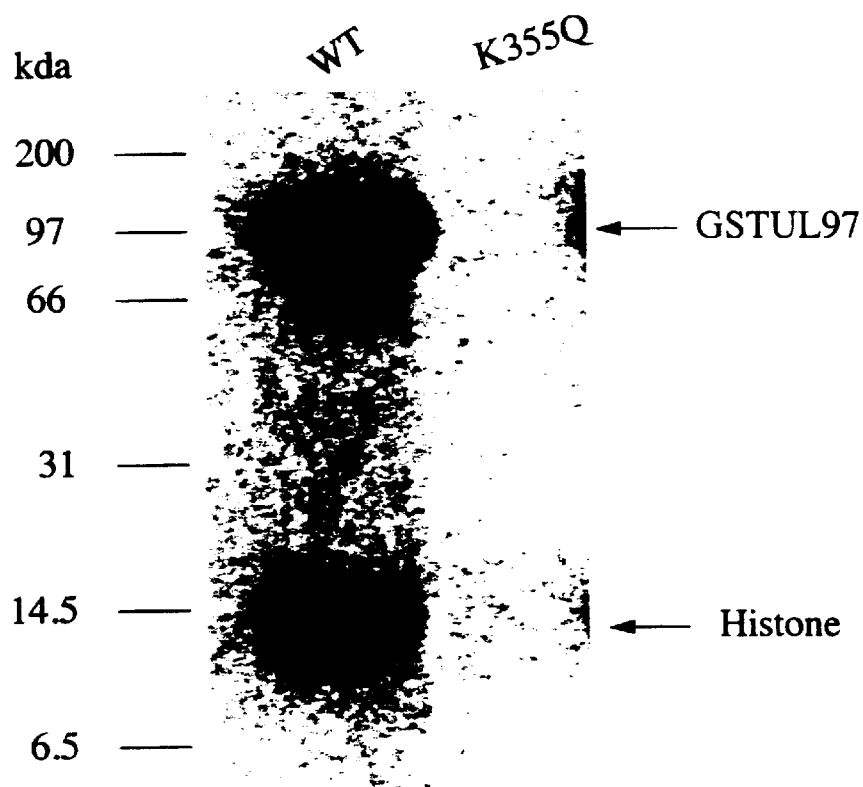
FIG. 11 is an autoradiograph of histone phosphorylated by GST-UL97.

GST-UL97 was tested in a kinase assay using various nonspecific potential kinase substrates, including myelin basic protein, casein, protamine, phosvitin, histone H1, histone H2B and a histone preparation consisting of a mixture of histones. Of these substrates, histones H1, H2B and the histone preparation were all phosphorylated. In a typical experiment, GST-UL97 (1.9 ng/µl) was incubated with histone (0.8 µg/µl) in 20 µl standard assay buffer. After a 30 min incubation at 37° C., the reaction was terminated by addition of SDS sample buffer. Proteins were resolved by electrophoresis on a 15% SDS-PAGE gel, and phosphorylation was detected by autoradiography. A representative autoradiograph is shown in FIG. 11. In the histone preparation, only one major phosphorylated species was detected. This 14.4 Kd species is histone H2B. The identification of the primary phosphorylated species in the histone preparation as histone H2B was confirmed using purified H2B (Boehringer Mannheim).

The optimal conditions for phosphorylation of the histone preparation were reevaluated, since the conditions may vary considerably with different substrates. In the presence of 10 mM $Mg^{2+}$, phosphorylation occurred most rapidly when the NaCl concentration was 0.4 to 0.8 M, and pH was between 8.6 and 9.1. Phosphorylation of histone occurred slowly relative to autophosphorylation of GST-UL97. In these experiments, the UL97 was preincubated with ATP for 60 min at room temperature. Histone (final concentration, 0.8 µg/µl) was added and the samples were incubated at 37° C. to initiate phosphorylation. Aliquots (10 µl) were removed at the indicated times, and boiled for 3 min with 10 µl 2×SDS sample buffer. After separation of phosphoproteins on 15% SDS-PAGE gels, the region corresponding to histone was excised and radioactivity counted. The histone phosphorylation reaction was not saturated at 60 min. The affinity constant ($K_m$) for histone was estimated to be 1.8±0.18 µM.

While the N-terminal regions of protein kinases are non-catalytic, they may affect enzymatic activity. Edelman et al., Rev. Diochem. 56:567–613 (1989); Pearson et al., Science 241:970–973 (1980). In order to investigate the effect of the N-terminal region of UL97 on phosphorylation, truncated parts of the UL97 ORF were cloned and expressed as GST fusion proteins, and analyzed for their ability to autophosphorylate and to phosphorylate histone in the same manner as GST-UL97. The truncated proteins were purified under the identical conditions as the GST-UL97 fusion proteins, and activity was assayed and quantified as described in Materials and Methods. These truncation mutants, ΔN103, ΔN238 and ΔN303, are missing the first 103, 238 and 303 amino acids of UL97, respectively, but they retain all of the UL97 sequences that align with the catalytic domains of known protein kinases. The results indicate that the truncation of the first 303 N-terminal amino acids totally abolishes enzymatic activity indicates that this region of UL97 is involved in kinase activity. While ΔN103 was impaired, it was still fairly active in phosphorylating both itself and histone. ΔN238 was more impaired for both activities than ΔN103, and ΔN303 was not detectably active. Since ΔN238 retained autophosphorylation activity while lacking the two identified autophosphorylation sites, either the remaining site is downstream of residue 238, or ΔN238 now recognizes a different site. The phenotype of the deletion mutants suggests that UL97 may be essential for CMV replication and, thus, that inhibitors of UL97 could serve as antiviral drugs. Homologs of UL97 found in other alpha herpesvirus can sustain deletions without major effects on viral replication in cultured cells, indicating that these UL97 homologs are not essential for viral replication. Coulter et al., J. Gen. Virol. 74:387–395 (1993); deWind et al., J. Virol. 66:5200–5209 (1992); Heineman et al., J. Virol. 69:7367–7370 (1995); Overton et al., Virology 202:97–106 (1994). Such mutations may nonetheless have important effects on viral pathogenesis.

TABLE 1

Effect of N-terminal truncation on phosphorylation

| Construct | autophosphorylation | histone phosphorylation |
|---|---|---|
| pGST-UL97 | ++++ | ++++ |
| pGST-UL97-K355Q | − | − |
| pGST-UL97-ΔN103 | ++ | +++ |
| pGST-UL97-ΔN238 | + | ++ |
| pGST-UL97-ΔN303 | − | − |

Identification of agents affecting UL97 protein kinase activity

The discovery that UL97 phosphorylates histone allows an assay to be developed for the detection of inhibitors or activators of UL97. In this assay, an agent which may be an inhibitor or an activator of UL97 is added to the phosphorylation reaction, and the reaction is allowed to proceed. The amount of phosphorylation is then measured, to see if the agent increases or decreases UL97-mediated histone phosphorylation.

Using this assay, the effect of several agents on the ability of UL97 to phosphorylate histone was examined. The results are shown in Table 1. Neither cAMP nor guanosine showed an inhibitory effect on GST-UL97 kinase activity, despite the fact that guanosine has been shown to inhibit the anabolism of GCV in cell cultures infected with recombinant vaccinia virus. Metzger et al., J. Virol. 68:8423–8427 (1994). Likewise, heparin, a potent inhibitor

TABLE 2

Effect of agents on GST-UL97 protein kinase activity in the histone phosphorylation assay

| Additions to reaction mixture | Activity (%) |
|---|---|
| none | 100 |
| spermine at 0.1 mM | 163 |
| Heparin at 0.1 mg/ml | 92 |
| ADP at 5 µM | 166 |
| cAMP at 5 µM | 115 |
| Guanosine at 10 µM | 125 |
| Quercetin at 10 µM | 28 |
| Tyrphostin 23 at 10 µM | 27 | of casein kinase II, had no effect on UL97 protein kinase activity.

ADP was also tested for its ability to affect UL97-mediated histone phosphorylation. ADP at 5 µM had a stimulatory effect on UL97 protein kinase activity. UL97-mediated phosphorylation of histone was also enhanced in the presence of 0.1 mM spermine.

The assay detected two agents which significantly reduced UL97-mediated histone phosphorylation. Quercetin at 10 µM reduced histone phosphorylation by more than 70%. Tyrphostins, which have been shown to be potent inhibitors of GTP-utilizing enzymes (Wolbring et al., J. Biol. Chem. 269:22470–22472 (1994)), were also tested for their ability to affect UL97 protein kinase activity. In the histone phosphorylation assay, as little as 10 µM tyrphostin 23 resulted in a 73% inhibition in phosphorylation.

What is claimed:

1. An assay for detecting an agent which inhibits the activity of UL97 protein kinase of CMV, said assay comprising the steps of:

a) providing a substrate for said protein kinase;
    b) incubating said substrate with UL97 protein kinase to form a substrate-protein kinase reaction mixture;
    c) adding a phosphate source;

d) adding a potential inhibitor of UL97 protein kinase activity to said reaction mixture;

d) measuring the amount of phosphorylation of said substrate in said reaction mixture; and e) comparing the amount of phosphorylation of said substrate detected in step (e) with the amount of phosphorylation detected in the absence of said potential inhibitor, as a measure of the inhibition of UL97 protein kinase activity.

2. The assay of claim 1, wherein the substrate is a histone preparation.

3. The assay of claim 1, wherein the substrate is a peptide containing a UL97 consensus phosphorylation sequence.

4. An assay for detecting an agent which enhances the activity of UL97 protein kinase of CMV, said assay comprising the steps of:

a) providing a substrate for said protein kinase;

b) incubating said substrate with UL97 protein kinase to form a substrate-protein kinase reaction mixture;

c) adding a phosphate source;

d) adding a potential enhancer of UL97 protein kinase activity to said reaction mixture;

e) measuring the amount of phosphorylation of said substrate in said reaction mixture; and f) comparing the amount of phosphorylation of said substrate detected in step (e) with the amount of phosphorylation detected in the absence of said potential enhancer, as a measure of the enhancement of UL97 protein kinase activity.

5. The assay of claim 4, wherein the substrate is a histone preparation.

6. The assay of claim 4, wherein the substrate is a peptide containing a UL97 consensus phosphorylation sequence.

7. A high throuput screen (HTS) for the detection of agents that inhibit or enhance UL97 protein kinase activity.

8. The HTS of claim 7, wherein the substrate is a peptide containing a UL97 consensus phosphorylation sequence.

9. An assay to detect a substrate for UL97 protein kinase, said assay comprising the steps of incubating a substance which may be a UL97 substrate with a UL97 protein kinase and a phosphate source, and detecting phosphorylation of said substance, said phosphorylation being an indication that said substance is a substrate for UL97 protein kinase.

10. An isolated nucleic acid encoding a UL97 fusion protein.

11. A vector comprising the nucleic acid of claim 10.

12. A cell containing the nucleic acid of claim 10.

13. A substantially pure preparation of a UL97 fusion protein.

14. A substantially pure antibody preparation that specifically binds UL97.

15. A kit for the detection of agents which inhibit or enhance UL97 protein kinase activity, said kit including a reaction vessel;

a substantially pure UL97 fusion protein; and a substrate that is known to be phosphorylated by UL97.

16. A substantially pure preparation of a peptide or a polypeptide comprising a UL97 phosphorylation consensus sequence.

17. The peptide or polypeptide of claim 16, wherein said peptide or polypeptide is modified.

18. A pharmaceutical composition for the treatment of CMV infection, said composition comprising a peptide or polypeptide according to claim 17.

19. A method of treating CMV infection, said method comprising administering a therapeutically effective amount of the composition of claim 18 to a CMV-infected individual.

* * * * *

UNITED STATES PATENT AND TRADEMARK OFFICE
CERTIFICATE OF CORRECTION

| | | |
|---|---|---|
| PATENT NO. | : 5,914,244 | Page 1 of 1 |
| APPLICATION NO. | : 08/910484 | |
| DATED | : June 22, 1999 | |
| INVENTOR(S) | : Coen et al. | |

It is certified that error appears in the above-identified patent and that said Letters Patent is hereby corrected as shown below:

In the Specification

At Column 1, Line number 11, please delete the paragraph and replace it with the following:
This invention was made with government support under AI026077 and AI033357 awarded by the National Institutes of Health. The government has certain rights in the invention.

Signed and Sealed this
Seventeenth Day of December, 2024

Derrick Brent
*Acting Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:1:

CGCGTGGTCC AGGTGGCGCG                                            20

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:2:

TTTGTTGAAG AATTCTCAAC AAA                                        23

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:3:

CGAGGATCCC CGCATGCGTT CGA                                        23

(2) INFORMATION FOR SEQ ID NO:4:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:4:

CCGGATCCCG GGCCCGGGCC GC                                         22

(2) INFORMATION FOR SEQ ID NO:5:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: oligonucleotide (xi) SEQUENCE DESCRIPTION: SEQ ID NO:5:

-continued

```
CGGGATCCGC GAGCTCTCTA TC                                            22
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

```
ATCGTCAGTC AGTCACGA                                                 18
```

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:7:

```
Asp Ile Thr Pro Met Asn
 1               5
```

(2) INFORMATION FOR SEQ ID NO:8:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (B) LOCATION: 2...2
        (D) OTHER INFORMATION: where Xaa at position 2 is Thr or Ser
        (B) LOCATION: 3...4
        (D) OTHER INFORMATION: where Xaa at positions 3 and 4 is any
            amino acid
        (B) LOCATION: 5...5
        (D) OTHER INFORMATION: where Xaa at position 5 is Tyr or Phe
        (B) LOCATION: 6...6
        (D) OTHER INFORMATION: where Xaa at position 6 is any amino
            acid (xi) SEQUENCE DESCRIPTION: SEQ ID NO:8:

```
Gly Xaa Xaa Xaa Xaa Xaa Ala Pro Glu
 1               5
```

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:9:

```
Tyr His Pro Ala Phe Arg Pro Met Pro
 1               5
```